(12) United States Patent
Allier et al.

(10) Patent No.: US 10,379,027 B2
(45) Date of Patent: *Aug. 13, 2019

(54) METHOD FOR IDENTIFYING BLOOD PARTICLES USING A PHOTODETECTOR

(71) Applicants: COMMISSARIAT A L'ENERGIE ATOMIQUE ET AUX ENERGIES ALTERNATIVES, Paris (FR); HORIBA ABX SAS, Montpellier (FR); IPRASENSE SAS, Clapiers (FR)

(72) Inventors: Cedric Allier, Grenoble (FR); Pierre Blandin, Coublevie (FR); Anais Ali Cherif, Montpellier (FR); Lionel Herve, Corenc (FR)

(73) Assignees: COMMISSARIAT A L'ENERGIE ATOMIQUE ET AUX ENERGIES ALTERNATIVES, Paris (FR); HORIBA ABX SAS, Montpellier (FR); IPRASENSE SAS, Clapiers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/560,763

(22) PCT Filed: Mar. 23, 2016

(86) PCT No.: PCT/FR2016/050643
§ 371 (c)(1),
(2) Date: Sep. 22, 2017

(87) PCT Pub. No.: WO2016/151248
PCT Pub. Date: Sep. 29, 2016

(65) Prior Publication Data
US 2018/0080760 A1   Mar. 22, 2018

(30) Foreign Application Priority Data
Mar. 24, 2015  (FR) .................................. 15 52443

(51) Int. Cl.
*G01N 15/14* (2006.01)
*G03H 1/08* (2006.01)
(Continued)

(52) U.S. Cl.
CPC ..... *G01N 15/1429* (2013.01); *G01N 15/1463* (2013.01); *G01N 21/453* (2013.01);
(Continued)

(58) Field of Classification Search
CPC ............. G01N 15/1429; G01N 21/453; G01N 15/1463; G01N 21/4788;
(Continued)

(56) References Cited

U.S. PATENT DOCUMENTS 9,970,858 B2   5/2018  Allier et al.
2008/0208511 A1*  8/2008  Trainer .............. G01N 15/0205
                                                                702/128
(Continued)

FOREIGN PATENT DOCUMENTS

WO   2014/012031 A1   1/2014

OTHER PUBLICATIONS

International Search Report dated Jun. 20, 2016 in PCT/FR2016/050643 filed Mar. 23, 2016.
(Continued)

*Primary Examiner* — Michael P LaPage
(74) *Attorney, Agent, or Firm* — Oblon, McClelland, Maier & Neustadt, L.L.P.

(57) ABSTRACT

A method for identifying a particle contained in a sample, including illuminating the sample using a light source, the light source producing an incident light wave propagating toward the sample, then acquiring, using a matrix-array photodetector, an image of the sample, the sample being placed between the light source and the photodetector such that the matrix-array photodetector is exposed to a light
(Continued)

wave that is the result of interference between the incident light wave and a diffraction wave produced by each particle. The method further includes applying a numerical reconstruction algorithm to the image acquired by the photodetector, to estimate a characteristic quantity of the light wave reaching the detector, at a plurality of distances from the detector. The variation in the characteristic quantity as a function of distance allows the particle to be identified.

15 Claims, 10 Drawing Sheets

(51) Int. Cl.
*G03H 1/04* (2006.01)
*G01N 21/45* (2006.01)
*G01N 21/47* (2006.01)
*G06K 9/00* (2006.01)
*G06T 7/00* (2017.01)
*G01N 33/49* (2006.01)

(52) U.S. Cl.
CPC ....... *G01N 21/4788* (2013.01); *G03H 1/0443* (2013.01); *G03H 1/0866* (2013.01); *G06K 9/00147* (2013.01); *G06T 7/0012* (2013.01); *G01N 33/49* (2013.01); *G01N 2015/1454* (2013.01); *G01N 2015/1488* (2013.01); *G03H 2001/0447* (2013.01); *G03H 2001/0883* (2013.01)

(58) Field of Classification Search
CPC ............ G01N 2015/1488; G01N 33/49; G06T 7/0012; G06K 9/00147
See application file for complete search history.

(56) References Cited

U.S. PATENT DOCUMENTS

| | | |
|---|---|---|
| 2009/0290156 A1 | 11/2009 | Popescu et al. |
| 2012/0105858 A1 | 5/2012 | Popescu et al. |
| 2012/0148141 A1 | 6/2012 | Ozcan et al. |
| 2013/0258091 A1 | 10/2013 | Ozcan et al. |
| 2013/0260396 A1* | 10/2013 | Akcakir ............. G01N 15/0211 435/7.25 |
| 2014/0016137 A1* | 1/2014 | Allier ................. G01B 9/02041 356/521 |
| 2014/0133702 A1 | 5/2014 | Zheng et al. |
| 2014/0327944 A1 | 11/2014 | Naidoo et al. |
| 2014/0365161 A1 | 12/2014 | Naidoo et al. |
| 2015/0204773 A1 | 7/2015 | Ozcan et al. |
| 2017/0045439 A1* | 2/2017 | Allier ................. G01N 15/1475 |

OTHER PUBLICATIONS

International Search Report dated Jul. 15, 2016 in PCT/FR2016/050644 filed Mar. 23, 2016.

Bjorn Kemper et al., "Application of 3D tracking, LED illumination and multi-wavelength techniques for quantitative cell analysis in digital holographic microscopy," Engineering of SPIE, SPIE-International Society for Optical Engineering, vol. 7184, Jan. 2009, XP007913134, pp. 1-12.

S. Vinjimore Kesavan et al., "High-throughput monitoring of major cell functions by means of lensfree video microscopy", Scientific Reports, vol. 4, Aug. 6, 2014, pp. 1-11, XP055250876.

Karen M. Molony et al., "Segmentation and visualization of digital in-line holographic microscopy of three-dimensional scenes using reconstructed intensity images", Medical Imaging 2002: PACS and Integrated Medical Information Systems: Design and Evaluation, vol. 7443, Aug. 20, 2009, pp. 74431 F-1-74431F-10, XP055251117.

Sergey Missan et al., "Using digital inline holographic microscopy and quantitative phase contrast imaging to assess viability of cultured mammalian cells", Progress in Biomedical Optics and Imaging, SPIE—International Society for Optical Engineering, vol. 9336, Mar. 11, 2015, pp. 93316X-1-93316X-14, XP060049373.

Yunxin Wang et al., "Non-invasive monitoring for living cell culture with lensless Fourier transform digital holography microscopy", Medical Imaging 2002: PACS and Integrated Medical Information Systems: Design and Evaluation, vol. 7791, Aug. 2, 2010, pp. 77910E-1-77910E-8, XP055250808.

Wu, Ning, et al., "Three-Dimensional Identification of Microorganisms Using a Digital Holographic Microscope", *Computational and Mathematical Methods in Medicine*, vol. 2013, 6 pages, 2013.

* cited by examiner

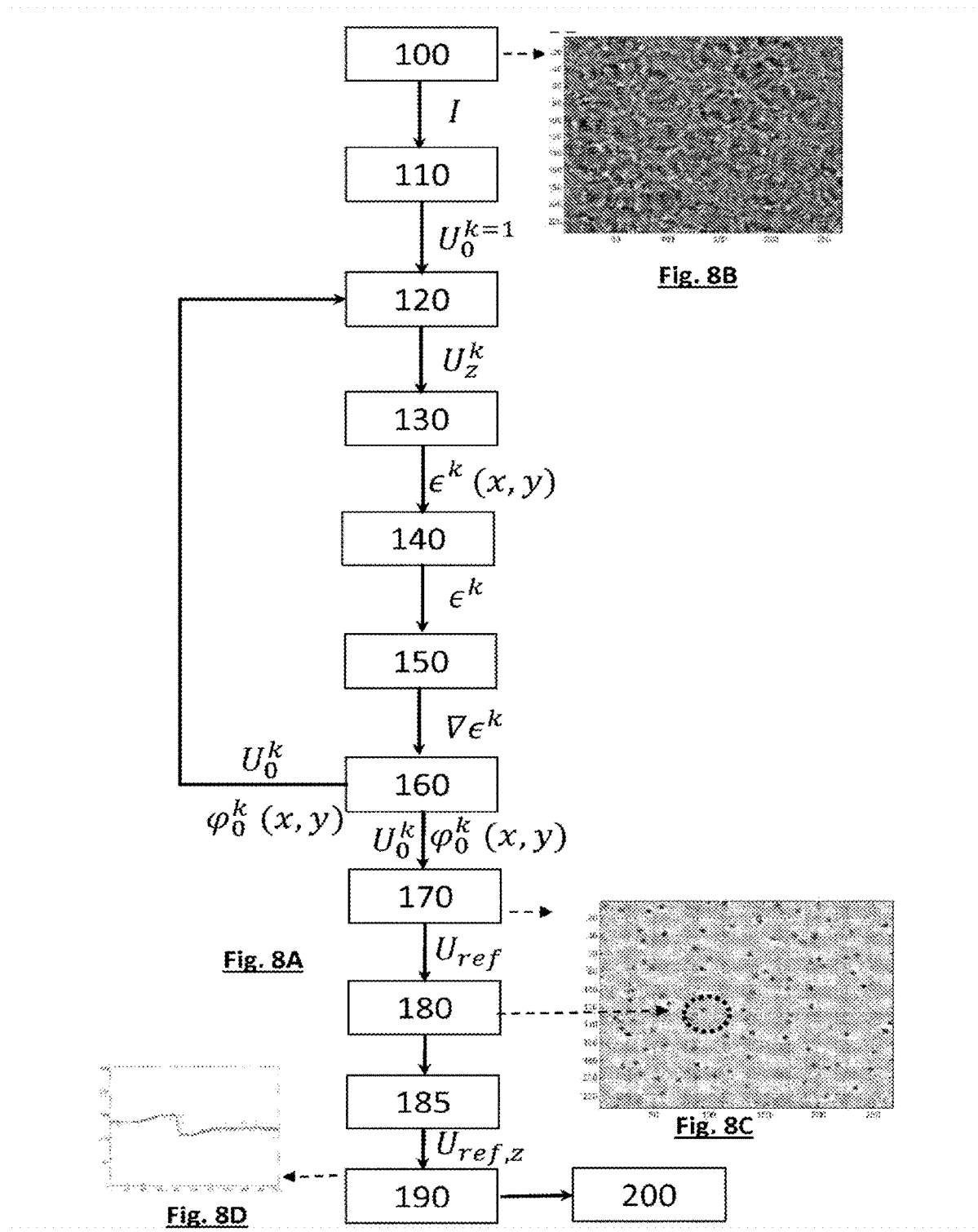

METHOD FOR IDENTIFYING BLOOD PARTICLES USING A PHOTODETECTOR

TECHNICAL FIELD

The invention relates to the field of counting and identifying particles present in a liquid and in particular in a bodily fluid, blood for example.

PRIOR ART

Bodily liquids, in particular blood, may contain particles, cells for example, the type and number of which it is useful to know.

For example, for blood, complete blood counts or full blood exams are tests commonly performed in medical laboratories. This type of test allows the main constituents (in particular the red blood cells, white blood cells, or platelets) of the blood and their number to be identified. These exams are commonly performed using high-performance automated devices, but simpler methods that are less expensive while still allowing comparable performance levels to be obtained are being researched.

One of the pursued avenues of research is the use of simple optical methods, such as lensless imaging. The observation of biological particles by lensless imaging has seen a certain amount of development since the end of the years 2000. This technique consists in placing a sample between a light source and a matrix-array photodetector or image sensor. The image captured by the photodetector is formed by interference between the incident wave, produced by the light source, and the wave diffracted by the particles making up the sample. This image is frequently referred to as a "hologram". Thus, for each particle, it is possible to record, on the sensor, a diffraction pattern that is specific thereto. Applied to biological samples, this technique has been described in document WO2008090330. It is then possible to perform a simple analysis of each particle, by comparing the diffraction pattern that it generates with diffraction patterns established beforehand and corresponding to known particles. However, this method may reach limits as particle concentration increases.

Specifically, counting and identifying particles solely on the basis of diffraction patterns detected by an image sensor reaches a certain limit as the concentration of particles in the sample increases. In particular, when the sample is blood, and the particles are red blood cells, beyond 100000 particles per µl, the count is no longer reliable, as was reported in the publication by Seo Sungjyu, "High-throughput lens-free blood analysis on a chip", Anal Chem, 2010, Jun. 1. It is possible to apply mathematical techniques i.e. what are referred to as digital holographic reconstruction techniques, in order to construct what is called a complex image of each particle present in the sample. This type of technique consists in back-propagating the light wave to the object plane, in which the particles are located, said object plane being located a known distance from the imager. The aforementioned publication demonstrates that such a holographic reconstruction allows red blood cells present in high concentrations in a sample to be counted. This publication reports that, in the reconstructed complex image, white blood cells having undergone marking beforehand have a different signature from that of red blood cells.

Document US2014/0327944 also describes a method for classifying particles, for example blood particles, on the basis of holograms, by comparing holograms acquired by an image sensor to a library of simulated holograms. However, this method shares the same limits, namely it becomes tricky to implement when particle density is high.

Methods allowing a complex image of cells (in this case spermatozoas) to be reconstructed are also described in documents US2012/0148141 and WO2014/012031. However, these methods allow the properties of said cells, and their path, to be estimated from the reconstructed complex image. The same goes for document US2009/0290156, which describes a classification of particles on the basis of a complex image of said particles, and of tracking of the path of said particles. A complex image of a sample may be insufficient to identify a particle.

A method for identifying particles, and in particular blood cells, that may be applied to samples in which particle concentration is high is sought. The method must moreover have a large field of observation and be simple to implement while in particular avoiding the need to mark particles beforehand. Moreover, the method musts allow particles liable to be found in a bodily fluid, and in particular red blood cells, white blood cells and platelets, to be reliably discriminated.

Moreover, a method not requiring precise knowledge of the distance between the particles and the photodetector is sought.

DISCLOSURE OF THE INVENTION

The invention responds to this problem, by providing a method for identifying a particle present in a sample, for example a sample of a biological liquid, such as blood, the method including the following steps:
  illuminating said sample using a light source, the light source producing an incident light wave propagating towards the sample along a propagation axis;
  acquiring, using a matrix-array photodetector, an image of the sample, the sample being placed between said light source and said photodetector in such a way that the matrix-array photodetector is exposed to a light wave comprising interference between the incident light wave and a diffraction wave produced by each particle;
the method being characterized in that it also comprises the following steps:
  determining a position of said particle in a plane parallel to a plane in which the matrix-array photodetector lies;
  applying a digital reconstruction algorithm to said acquired image, so as to estimate at least one characteristic quantity of said light wave to which the matrix-array photodetector is exposed, at a plurality of reconstruction distances from the latter;
  determining a profile, representing a variation in said characteristic quantity as a function of said reconstruction distance, along an axis parallel to said propagation axis and passing through said position; and
  identifying the particle depending on said profile.

By applying a digital reconstruction algorithm, what is meant is the application of a propagation operator to an image, generally in the form of a convolution product.

The characteristic quantity may be obtained by estimating, at each reconstruction distance, a complex expression of the light wave to which the matrix-array photodetector is exposed.

The characteristic quantity may be determined from the modulus of said complex expression, in which case it is representative of the amplitude of said light wave to which the detector is exposed.

The characteristic quantity may be determined from the argument of said complex expression, in which case it is representative of the phase of said light wave to which the matrix-array photodetector is exposed.

According to one embodiment, the method includes:

determining a complex image called the reference complex image by applying a digital reconstruction algorithm to the image acquired by the matrix-array photodetector;

from said reference complex image, estimating at least one characteristic quantity of the light wave to which the matrix-array photodetector is exposed, at a plurality of reconstruction distances from the latter.

The method may then include:

applying a propagation operator to the reference complex image, so as to calculate what are called secondary complex images for a plurality of distances from the reconstruction plane or from the plane in which the matrix-array photodetector lies;

determining a characteristic quantity at each of said distances, from each secondary complex image.

The reference complex image may be a complex image formed in a reconstruction plane that is away from the plane of the sample. It may also be a question of a complex image formed in the detection plane.

The identification may be achieved by comparing the variation in said characteristic quantity to reference profiles determined in a learning phase.

The position of each particle, in a plane parallel to the plane of the matrix-array photodetector, may be determined using the image acquired by the photodetector or using the complex expression of the light wave to which the photodetector is exposed.

The light source is preferably a spatially coherent source, and for example a light-emitting diode, in which case a spatial filter is preferably placed between the light source and the sample. The light source may be temporally coherent, by being for example a laser diode.

The matrix-array photodetector includes a matrix array of pixels that are able to collect the wave to which the photodetector is exposed. The distance between the pixels and the sample may vary between 50 µm and 2 cm, and preferably between 100 µm and 5 mm. Preferably the sample is not placed in direct contact with the pixels of the photodetector.

Preferably, no magnifying optics are placed between the sample and the matrix-array photodetector.

The sample may in particular include blood cells. In this case, the particles may be identified among cell lines of white blood cells, red blood cells or platelets.

Another subject of the invention is a device for identifying a particle, said particle being contained in a sample, the device comprising:

a light source that is arranged to produce an incident light wave, along a propagation axis, in the direction of said sample; and a holder, for holding the sample between said light source and a matrix-array photodetector;

the matrix-array photodetector, which is arranged to acquire an image of the sample, being able to be exposed to a light wave resulting from interference between said incident light wave and a diffraction wave formed by said particle;

characterized in that the device includes a processor, such as microprocessor or electronic computer, configured to implement the following operations:

determining a position of said particle in a plane parallel to the plane of the matrix-array photodetector;

applying a digital reconstruction algorithm to said acquired image, so as to estimate at least one characteristic quantity of said light wave to which the matrix-array photodetector is exposed, at a plurality of reconstruction distances from the latter;

determining a profile, representing the variation in said characteristic quantity as a function of said reconstruction distance, along an axis parallel to said propagation axis and passing through said position; and identifying the particle depending on said profile.

Preferably, the device includes no magnifying optics between the matrix-array photodetector and the analyzed sample.

The processor may include or be connected to a programmable memory, comprising a sequence of instructions allowing the steps described above to be implemented.

It may in particular be able:

to determine, at each reconstruction distance, the complex expression of the optical radiation to which the detector is exposed; and to estimate said characteristic quantity, at each reconstruction distance, by determining the modulus or argument of said complex amplitude.

FIGURES

FIGS. 8A, 8B, 8C and 8D respectively show:
a method allowing a complex image, called the reference complex image, of a sample to be calculated in a reconstruction plane;
a hologram acquired by the matrix-array photodetector;
a representation of an image, called a reference complex image, reconstructed after a plurality of iterations of the method shown in FIG. 8A; and
a profile obtained on the basis of secondary complex images formed from the reference complex image.

Figure 9A:
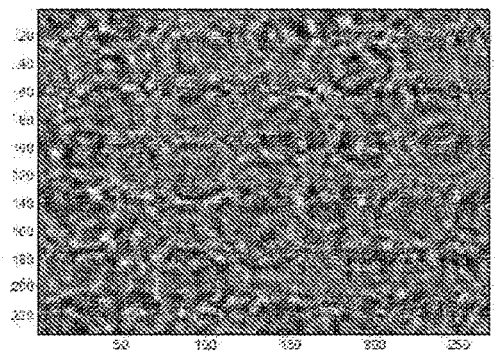
Figure 9B:
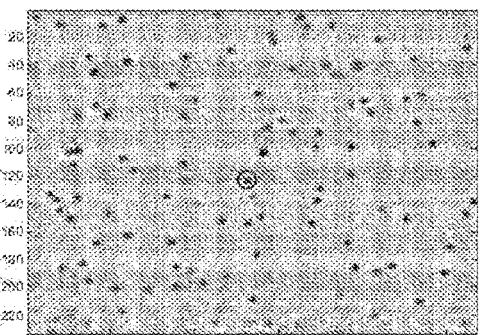
Figure 9C:
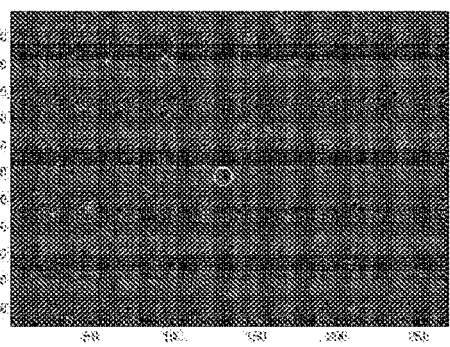
Figure 9D:
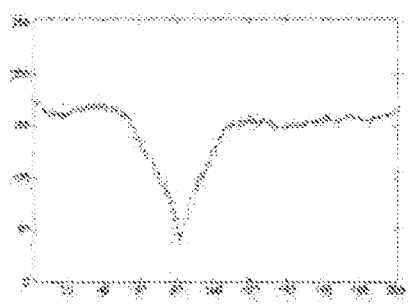
Figure 9E:
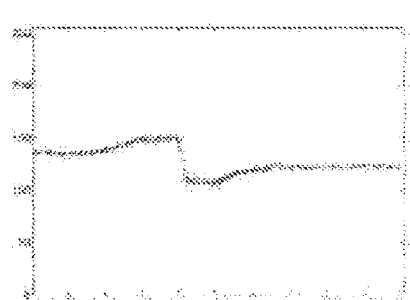

FIG. 9A is a hologram acquired by an image sensor, the sample including red blood cells dispersed in an aqueous solution. FIGS. 9B and 9C respectively show the modulus and phase of a complex image that is what is called a reference image, this complex image being formed in a reconstruction plane. FIGS. 9D and 9E are profiles respectively showing a variation in the modulus and phase of the light wave to which the image sensor is exposed, along a propagation axis passing through a red blood cell.

DISCLOSURE OF PARTICULAR EMBODIMENTS

Figure 1:
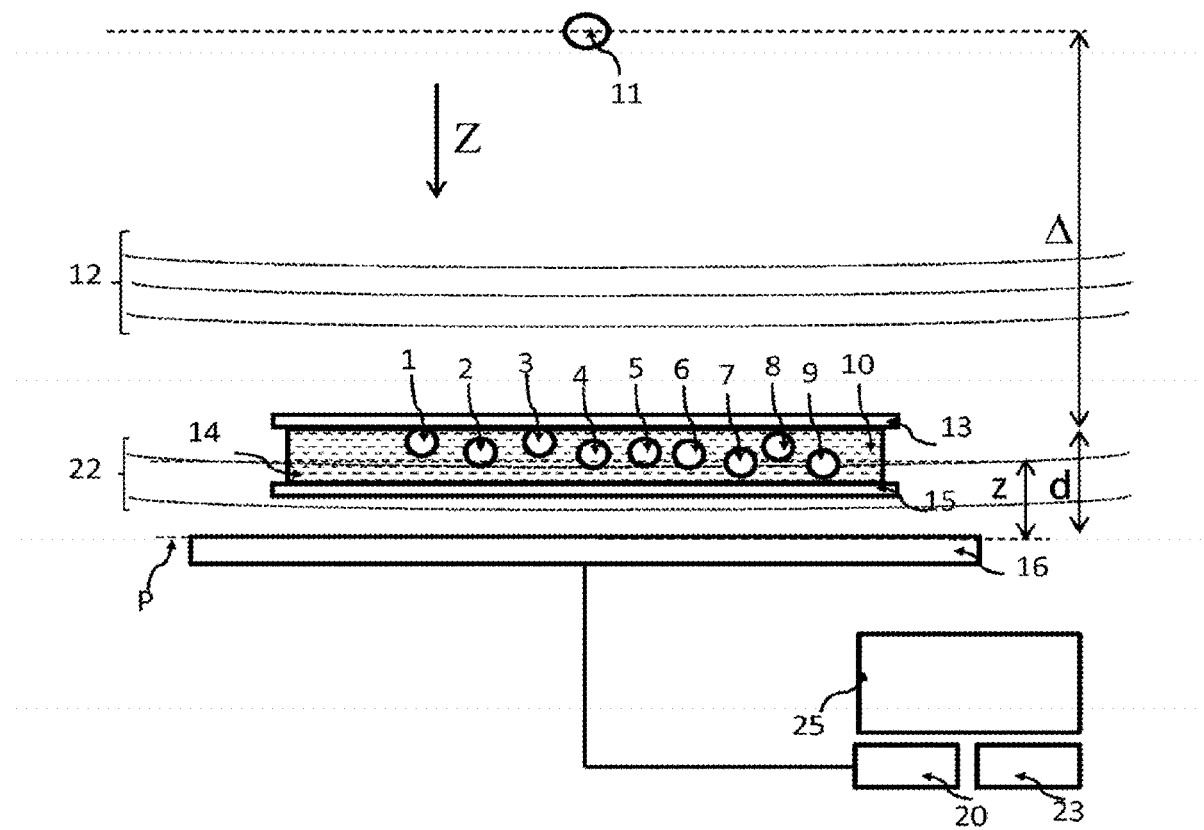
FIG. 1 shows the device according to one embodiment of the invention.

FIG. 1 shows an example of the device that is one subject of the invention.

A light source 11 is able to produce a light wave 12, which is called the incident light wave, in the direction of a sample 14, along a propagation axis Z. The sample 14 includes a medium 10, for example a biological liquid, including particles 1, 2, 3, 4, 5, . . . , 9 that it is desired to identify among preset types of particles.

A particle may be a cell. In particular, when the medium 10 is blood, or a solution including blood, a particle may be a red blood cell, a white blood cell or a platelet.

A particle may also be an organic or inorganic microbead, for example a metal microbead or a microbead of polymer or glass, this type of microbead commonly being used when performing biological protocols. A particle may also be a droplet, for example a lipid droplet, immersed in the medium 10. It may also be a question of a microorganism, for example a bacterium or a yeast, or of an exosome. Generally, a particle has a size advantageously smaller than 1 mm, even smaller than 500 µm, and preferably a size comprised between 0.5 µm and 500 µm. Thus, the term particle refers both to endogenic particles initially present in the examined sample, and exogenic particles that are added to this sample before analysis.

The medium 10 is most frequently a liquid medium, and in particular a bodily liquid, but it may also be a question of an agar, or air, or the dry residue of a liquid.

The method that is one subject of the invention allows each observed particle to be identified. By identification, what is meant is the classification of the particle into a preset class of particles. It may be a question of determining a nature of a particle among preset natures, or of determining a size of a particle among preset natures.

The distance Δ between the light source and the sample is preferably larger than 1 cm. It is preferably comprised between 2 and 30 cm. Preferably, the light source, seen by the sample, may be considered to be point-like. This means that its diameter (or its diagonal) is preferably smaller than one tenth and better still one hundredth of the distance between the sample and the light source. Thus, the light reaches the sample in the form of plane waves, or waves that may be considered as such.

The light source 11 may be a point light source, or be associated with a diaphragm or spatial filter (not shown in FIG. 1) so as to appear point-like. The aperture of the diaphragm is typically comprised between 5 µm and 1 mm and preferably between 50 µm and 500 µm.

The diaphragm may be replaced by an optical fiber, a first end of which is placed facing a light source, and a second end of which is placed facing the sample. In this case, said second end may be likened to a point light source 11.

The sample 14 is bounded by a chamber, including a base 15 and a cover 13. The side walls of the chamber have not been shown. In the considered example, the chamber is a Neubauer C-chip fluidic chamber. The distance between the base 15 and the cover 13 is 100 µm. Generally, the thickness of the chamber, along the propagation axis Z, is smaller than a few cm, for example smaller than 1 cm, or even smaller than 1 mm, and for example comprised between 50 µm and 500 µm.

The light source 11 may be temporally coherent but this is not necessary.

In this first example, the light source is a laser diode emitting at a wavelength of 450 nm. It is located a distance of 15 cm from the sample.

The sample 14 is placed between the light source 11 and a matrix-array photodetector or image sensor 16. The latter preferably extends parallelly, or substantially parallelly, to the base 15 of the chamber bounding the sample.

The expression substantially parallelly means that the two elements may not be rigorously parallel, an angular tolerance of a few degrees, smaller than 10°, being acceptable.

Preferably, the light source is of small spectral width, for example of spectral width smaller than 100 nm or even 20 nm and even preferably smaller than 5 nm. The expression spectral width designates the full width at half maximum of the emission peak of the light source.

The photodetector 16 may be a matrix-array photodetector including a matrix-array of CCD or CMOS pixels. CMOS photodetectors are preferred because the size of the pixels is smaller, this allowing images the spatial resolution of which is more favorable to be acquired. In this example, the detector is a 12-bit APTINA sensor of reference MT9P031. It is a question of an RGB CMOS sensor the inter-pixel pitch of which is 2.2 µm. The useful area of the photodetector is 5.7×4.3 mm$^2$.

The photodetector lies in a detection plane P that is preferably perpendicular to the propagation axis Z of the incident light wave 12.

Preferably, the photodetector comprises a matrix-array of pixels, above which array a transparent protective window is placed. The distance between the matrix-array of pixels and the protective window is generally comprised between a few tens of µm to 150 or 200 µm. Photodetectors the inter-pixel pitch of which is smaller than 3 µm are preferred, in order to improve the spatial resolution of the image.

The distance d between the particles 1, 2, . . . 9 and the matrix-array of pixels of the photodetector 16 is, in this example, equal to 1.5 mm. However it may fluctuate depending on the thickness of the fluidic chamber used. Generally, and whatever the embodiment, the distance d between a particle and the pixels of the photodetector is preferably comprised between 50 µm and 2 cm and preferably comprised between 100 µm and 2 mm.

The absence of magnifying optics between the matrix-array photodetector 16 and the sample 14 will be noted. This does not prevent focusing micro-lenses optionally being present level with each pixel of the photodetector 16.

In this first example, the sample is white-blood-cell-rich plasma obtained according to a conventional protocol, after sedimentation of the red blood cells in the presence of 6% Dextran (Sigma Aldrich reference D4876) in Alsever's solution, then collection of the platelet- and white-blood-cell-rich plasma. The plasma obtained is then diluted in a phosphate-buffered saline (PBS) buffer at physiological pH. The depletion of the red blood cells is not complete and the rich plasma obtained contains residual red blood cells.

The particles may be classified among a number of types of particles, and in particular red blood cells, white blood cells or platelets. Preferably, the particles undergo no marking beforehand.

Figure 2A:
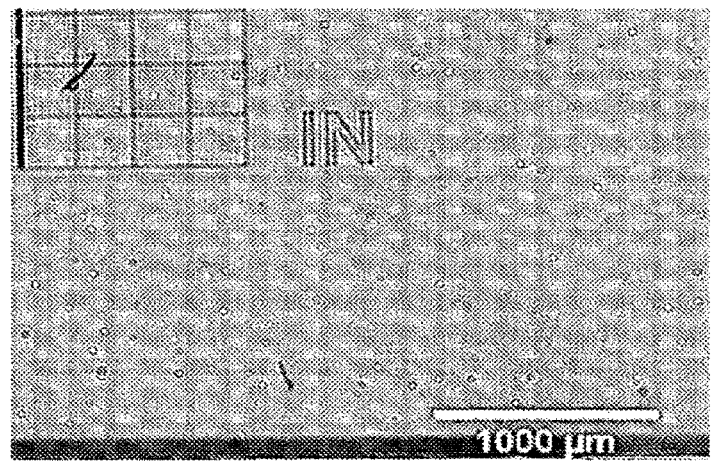
FIG. 2A shows an image acquired by the matrix-array photodetector.

FIG. 2A shows an image obtained by the photodetector 16. This image shows an overall diffraction pattern, in which elementary diffraction patterns, each elementary diffraction pattern being associated with respective particles, may be seen. Each elementary diffraction pattern comprises a central disc-shaped zone, around which alternately dark and light concentric rings extend. Such an elementary pattern allows a particle to be identified to be selected, and the what are called radial coordinates (x,y) of said particle in the detection plane P to be determined. These coordinates are for example the center of the elementary diffraction pattern corresponding to said particle.

Each elementary diffraction pattern is formed by the interference between the incident light wave 12 produced by the source 11, upstream of the sample, and a wave resulting from the diffraction of the incident wave by a particle. Thus, the photodetector 16 is exposed to a light wave 22 formed by the superposition:
- of the light wave 12 emitted by the source 11, upstream of the sample 14; and
- of the light wave diffracted by each of the particles or other diffracting elements present in the sample 14.

A processor 20, for example a microprocessor, receives the images of the matrix-array photodetector 16, and performs a reconstruction of characteristic quantities of the light wave 22 to which the matrix-array photodetector is exposed, along the propagation axis Z. The microprocessor 20 is connected to a memory 23 able to store instructions for implementing the calculating steps described in this application. It may be linked to a screen 25. The reconstruction is in particular created between the matrix-array photodetector and the observed sample.

The processor 20 may be able to execute a sequence of instructions stored in a memory, in order to implement steps of the identifying method. The processor may be a microprocessor, or any other electronic computer able to process the images delivered by the matrix-array photodetector, in order to execute one or more steps described in this description.

The image I acquired by the matrix-array photodetector, which image is shown in FIG. 2A, represents the spatial distribution of the intensity I(x,y) of the light wave 22, x and y being the coordinates in the plane P of the photodetector.

According to well-known digital holographic reconstruction principles, which are described in the publication by Ryle et al, "Digital in-line holography of biological specimens", Proc. of SPIE Vol. 6311 (2006), it is possible to reconstruct a complex expression U(x,y,z) for the light wave 22 at any point of spatial coordinates (x,y,z), and in particular in a plane located a distance |z| from the photodetector, by determining the convolution product of the intensity I(x,y) measured by the photodetector and a propagation operator h(x,y,z).

The function of the propagation operator h(x,y,z) is to describe the propagation of the light between the photodetector 16 and a point of coordinates (x,y,z). It is then possible to determine the amplitude u(x,y,z) and the phase φ(x,y,z) of this light wave at this distance |z|, which is called the reconstruction distance, where:

$$u(x,y,z)=\text{abs}[U(x,y,z)];$$

$$\varphi(x,y,z)=\arg[U(x,y,z)]$$

The operators abs and arg return the modulus and argument, respectively.

Application of the propagation operator in particular allows the complex expression to be estimated at a distance |z| from the photodetector, upstream of the latter. The complex value of the light wave 22 before the latter reaches the detector is thus reconstructed. Back-propagation is then spoken of. If the coordinate z=0 is attributed to the detection plane P, this back-propagation is implemented by applying a propagation operator h(x,y,−|z|). The terms upstream and downstream are to be understood with respect to the propagation direction of the incident wave 12.

If I(x,y)=I(x,y,z=0) corresponds to the intensity of the signal measured by the photodetector, the relationship between the measured intensity I(x,y) and the complex expression U(x,y) of the light wave, in the detection plane P, is given by: I(x,y)=|U(x,y)|*.

The complex expression of the light wave (22), at a coordinate (x,y,z), is given by:

$$U(x,y,z)=\sqrt{I(x,y)}*h(x,y,z), \text{ the symbol } * \text{ representing a convolution operator.}$$

where:
- z<0 in the half-space delineated by the detection plane P and comprising the sample 14; and
- z>0 in the half-space delineated by the detection plane P and not comprising the sample 14.

In the half-space delineated by the detection plane P and comprising the sample 14, the complex expression of the light wave may also be written:

$$U(x,y,z)=\sqrt{I(x,y)}*h(x,y,-|z|).$$

Preferably mathematical preprocessing is applied beforehand to the measured intensity I(x,y), before the holographic reconstruction. This allows the quality of the results to be improved, in particular by decreasing the number of artefacts created when the propagation operator is applied.

Thus, an intensity Ĩ(x,y), called the normalized intensity, is determined, such that $$\tilde{I}(x,y)=(I(x,y)-\text{Average}(I))/\text{Average}(I)$$

where
- I(x,y)=intensity measured by the photodetector at the coordinate (x,y);
- Average (I)=average of the intensity measured in a region of interest of the image I, including said coordinate (x,y). This region of interest may correspond to the entire image formed by the photodetector.

This pre-processing is equivalent to a normalization of the measured intensity by the intensity of the incident light wave (12), the latter intensity being estimated by the operator Average (I).

Next, the complex expression of the wave (22) is determined from the normalized intensity Ĩ(x,y) using the equation $U(x,y,z)=\sqrt{\tilde{I}(x,y)}*h(x,y,z)$ as explained above.

The digital reconstruction may in particular be based on the Fresnel diffraction model. In this example, the propagation operator is the Fresnel-Helmholtz function, such that:

$$h(x, y, z) = \frac{1}{j\lambda z} e^{j2\pi \frac{z}{\lambda}} \exp\left(j\pi \frac{x^2 + y^2}{\lambda z}\right),$$

where $\lambda$ is the wavelength.
Thus, $$U(x, y, z) = \frac{1}{j\lambda z} e^{j2\pi \frac{z}{\lambda}} \int\int \sqrt{I(x', y')} \exp\left(j\pi \frac{(x-x')^2 + (y-y')^2}{\lambda z}\right) dx' dy'$$

where
x' and y' are the coordinates in the plane of the photodetector;
x and y are the coordinates in the reconstruction plane, the latter being located at a distance |z| from the photodetector;
z is the coordinate of the reconstructed image along the propagation axis Z of the incident light wave (12).

From the values of the complex expression U(x,y,z), it is possible to extract characteristic quantities of the light wave 22 resulting from the diffraction, by the particles (1, 2 . . . 9), of the incident light wave 12 emitted by the source 11. As mentioned above, it is possible to evaluate the amplitude u(x,y,z) or the phase φ(x,y,z), but it is also possible to evaluate any function of the amplitude or phase.

It is for example possible to evaluate a characteristic quantity that is called the complementary amplitude ũ(x,y,z) such that:

ũ(x,y,z)=abs(1−U(x,y,z))

From each reconstructed complex expression U(x,y,z), it is possible to form:
an image $u_z$ of the amplitude of the wave 22, in a plane parallel to the plane of the detector, at a distance |z| from the latter, where $u_z(x,y)=abs[U(x,y,z)]$;
an image $\varphi_z$ of the phase of the wave 22, in a plane parallel to the plane of the detector, at a distance |z| from the latter, where $\varphi_z(x,y)=arg[U(x,y,z)]$;
an image $\tilde{u}_z$ of the complementary amplitude, such as described above, of the wave 22, in a plane parallel to the plane of the detector, at a distance |z| from the latter, where $\tilde{u}_z(x,y,z)=abs[1-U(x,y,z)]$.

In this first example,
an image $\tilde{u}_z$ of the complementary amplitude is reconstructed at a plurality of coordinates $z_1 \ldots z_M$, along the propagation axis Z, M here being equal to 21;
from each image $\tilde{u}_{zm}$, where $1 \leq m \leq M$, the value $\tilde{u}(x_n, y_n, z_m)$ is extracted, $(x_n, y_n)$ representing the coordinates of the particle n in a plane parallel to the plane of the photodetector 16; and
various values of $\tilde{u}(x_n, y_n, z)$, where $z_m < z < z_{m+1}$, are obtained by interpolation between two quantities $\tilde{u}(x_n, y_n, z_m)$ and $\tilde{u}(x_n, y_n, z_{m+1})$ determined beforehand.

The coordinates $(x_n, y_n)$, in a plane parallel to the plane of the photodetector 16, of each examined particle n, are determined either using the acquired image I(x,y) or from an image $\tilde{u}_z$ at a given reconstruction height z.

Figure 2B:
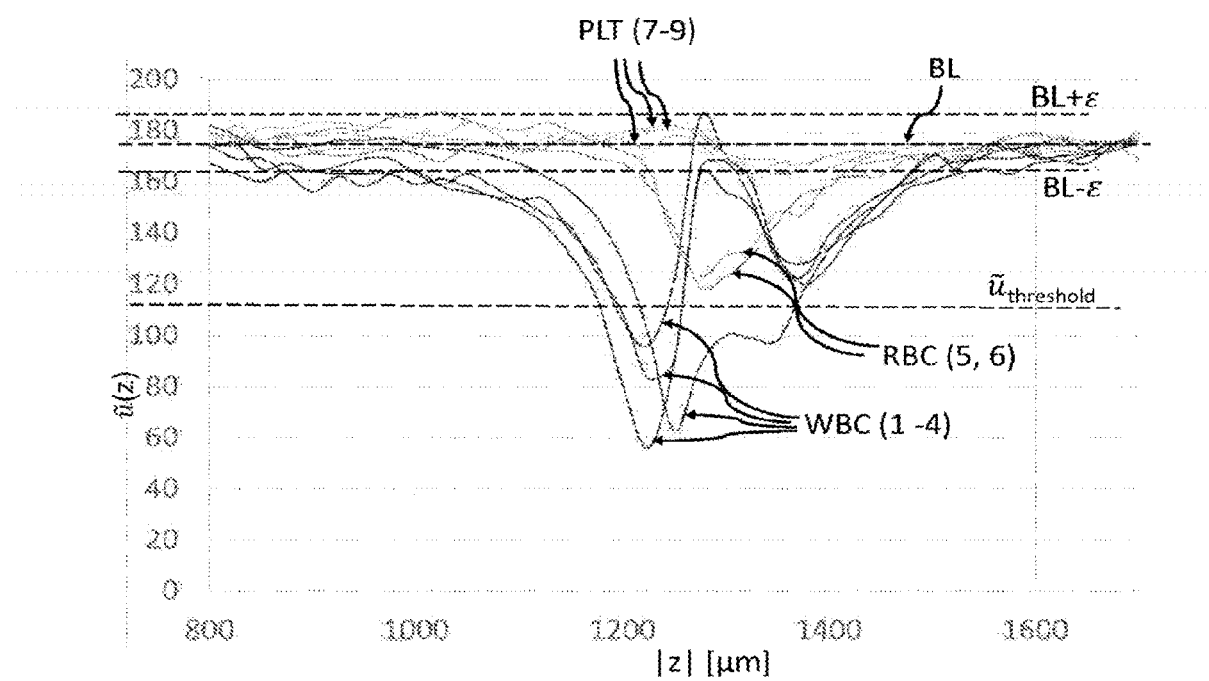
FIG. 2B shows the profile of a characteristic quantity, called the complementary amplitude, of the light wave to which the photodetector is exposed, as a function of distance with respect to the photodetector, according to a first example, for various types of particles.

FIG. 2B shows, for various types of particles, the variation in the complementary amplitude ũ($x_n, y_n, z$), such as defined above, as a function of the reconstruction distance |z| for 9 different particles:

particles 1 to 4: white blood cells designated by the acronym WBC;
particles 5 and 6: red blood cells designated by the acronym RBC; and
particles 7 to 9: platelets, designated by the letters PLT.

The reconstruction distance |z| varies between $z_{min}$=1000 and $z_{max}$=1500 μm.

Parallelly to these operations, each particle (1, . . . , 9) was observed under a microscope, the observation under microscope serving as a reference measurement, allowing an indisputable identification to be obtained.

In the sample studied in this example it may be seen that:
for particles 1 to 4, which are white blood cells WBC, the curve u(z) representing the variation in the complementary amplitude as a function of reconstruction distance has a minimum lower than an amplitude threshold $\tilde{u}_{threshold}$, followed by an increase toward the baseline BL, this increase having marked oscillations;
for particles 5 and 6, corresponding to red blood cells RBC, the curve ũ (z) has a minimum comprised between the baseline BL and the amplitude threshold $\tilde{u}_{threshold}$, followed by a monotonic increase to the baseline BL; and
for particles 7 to 9, corresponding to platelets PLT, the curve ũ(z) follows the baseline BL and remains confined between two values BL±ε.

Thus, for each detected particle n, the position of which in a plane parallel to the plane of the detector is $(x_n, y_n)$, it is possible to establish a profile $\tilde{u}(x_n, y_n, z)$ representing the variation in the complementary amplitude at a plurality of reconstruction heights z, and to use this profile to identify whether the particle is a red blood cell, a white blood cell or a platelet.

This profile may in particular be compared to a library of profiles produced, in a learning phase, with known particles. In other words, the profile ũ(z) representing the variation in the complementary amplitude, along the propagation axis Z (axis of the coordinates z), forms a signature of the type of particle observed.

In contrast to the prior art, a complex image of a particle is not formed by performing a holographic reconstruction at a preset distance from the sample, but rather a characteristic of the wave 22 resulting from the diffraction of a particle with the incident wave 12 is reconstructed along the propagation direction of the incident wave, at a plurality of distances from the photodetector. The information obtained is richer and allows a clear classification between various types of particles.

Figure 3A:
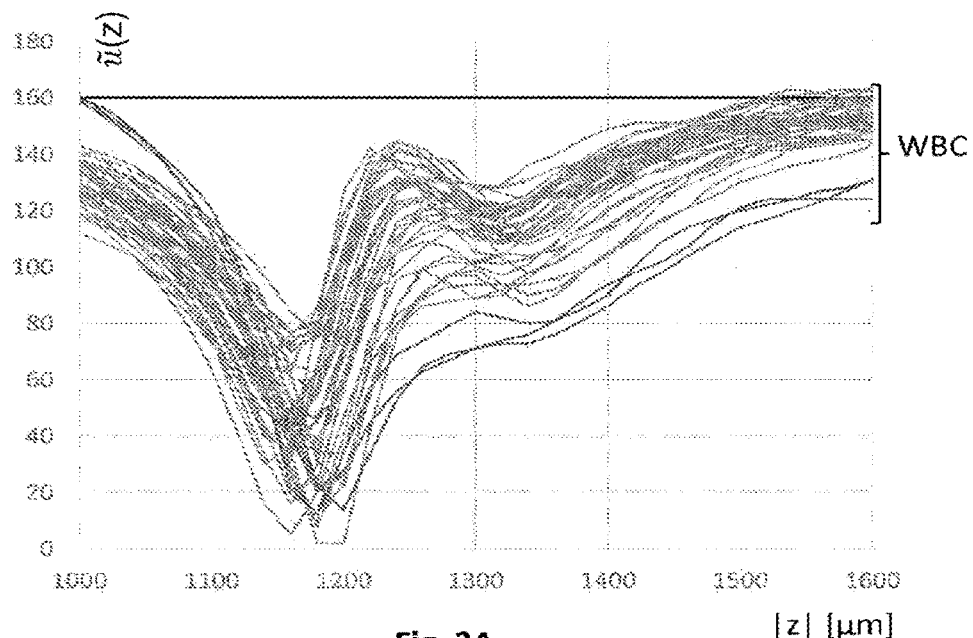
FIG. 3A shows the profile of a characteristic quantity, called the complementary amplitude, of the light wave to which the photodetector is exposed, as a function of distance with respect to the photodetector, for various white blood cells, according to this first example.
Figure 3B:
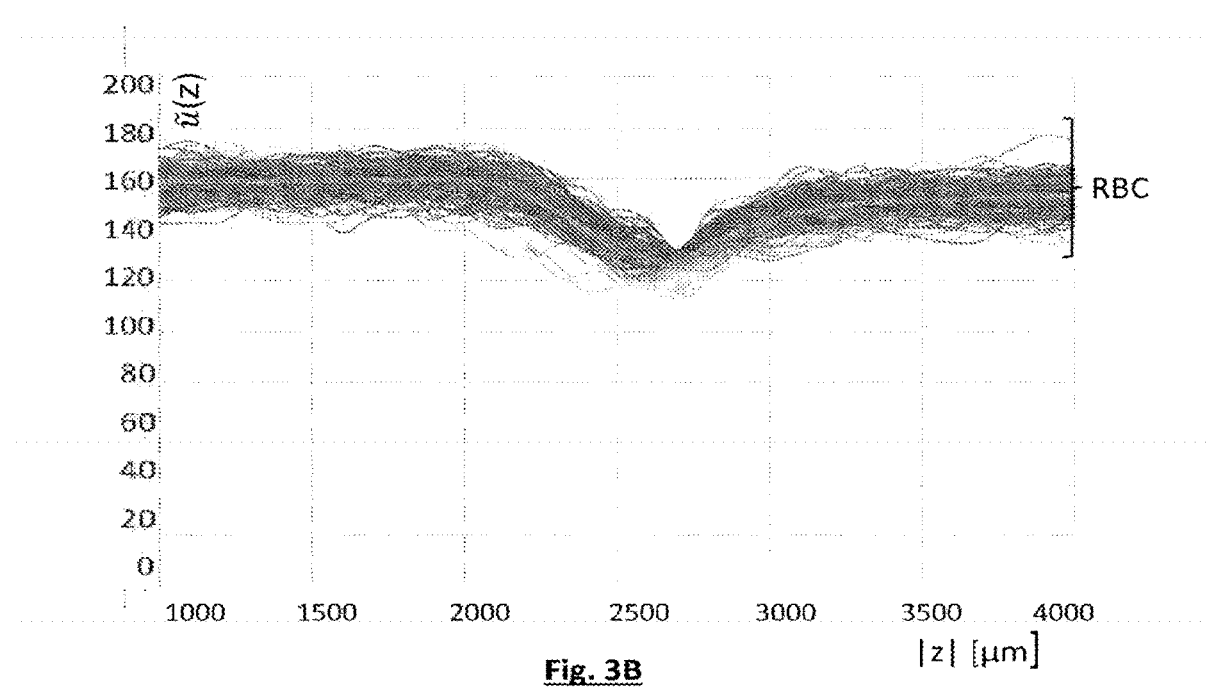
FIG. 3B shows the profile of a characteristic quantity, called the complementary amplitude, of the light wave to which the photodetector is exposed, as a function of distance with respect to the photodetector, for various red blood cells, according to this first example.

FIGS. 3A and 3B show complementary-amplitude profiles ũ (z) of the wave 22 to which the detector is exposed, said profiles being obtained for 50 white blood cells WBC and 240 red blood cells RBC, respectively. The repeatability of the profiles is sufficient to allow robust classification of particles on the basis thereof. These profiles were obtained under experimental conditions analogous to those of the preceding example.

The sample used to obtain the measurements shown in FIG. 3A was a rich plasma similar to the sample described with reference to FIGS. 2A and 2B.

The sample used to obtain the measurements shown in FIG. 3B included total blood diluted with a dilution factor of 1/400 in a phosphate-buffered saline (PBS) buffer such as mentioned above.

Figure 4A:
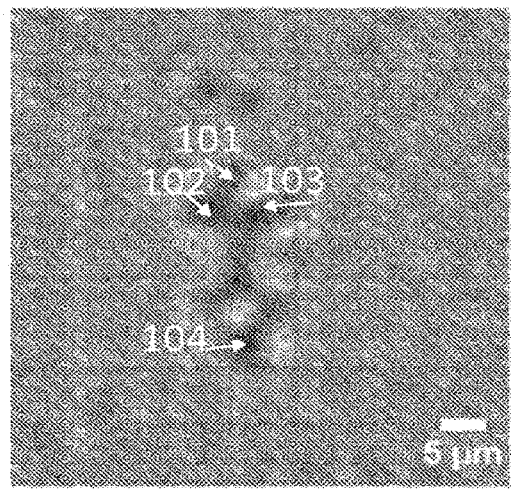
FIG. 4A shows a region of interest of the image acquired by the photodetector, which is centered on a platelet aggregate, according to this first example.
Figure 4B:
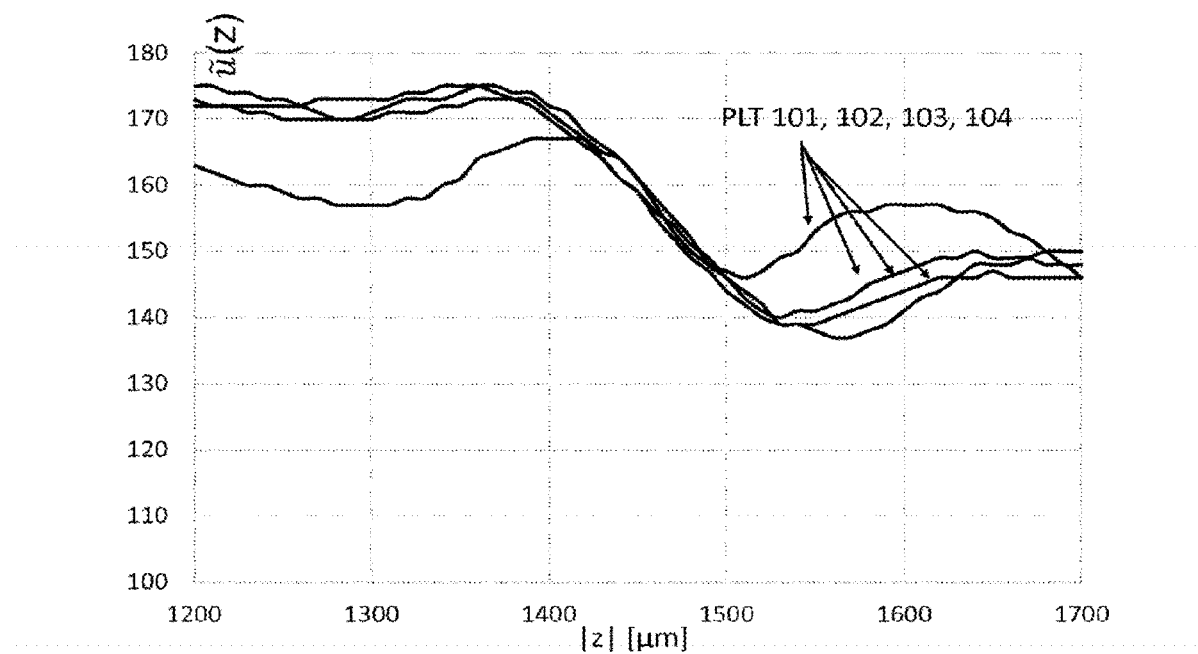
FIG. 4B shows the profile of a characteristic quantity, called the complementary amplitude, of the light wave to which the photodetector is exposed, for various platelets forming part of the aggregate shown in FIG. 4A.

FIG. 4B shows complementary-amplitude profiles ũ (z) obtained, along the axis Z, for 4 platelets 101, 102, 103, 104, in a sample of rich plasma of the type described above.

Observation under microscope showed that the platelets 101, 102, 103 and 104 were aggregated.

FIG. 4A shows a region of interest of the image I acquired by the photodetector 16. It allows the coordinates ($x_{101}$, $y_{101}$), ($x_{102}$,$y_{102}$), ($x_{103}$,$y_{103}$), ($x_{104}$,$y_{104}$) of each platelet of the aggregate to be identified.

These profiles were obtained under experimental conditions analogous to those of the first example. It may be seen that the profile ũ (z) is similar whether the platelets are aggregated or not, and remains confined about a baseline BL, within an interval BL±ε. Thus, with the identifying method that is one subject of the invention, platelets are correctly identified even if they are aggregated.

In a second example, the light source 11 is a white light-emitting diode coupled to a 485-DF-22 Omega Optical filter centered on the wavelength λ=485 nm and of full width at half maximum equal to 22 nm. The distance Δ between the light source and the detector is equal to 8 cm. The sample is a rich plasma such as described above.

In this example, the complex expression U(x,y,z) of the wave 22 was reconstructed at a plurality of distances z from the detector, and then, at the coordinates (x,y) of various particles, the complementary amplitude and phase of the radiation were determined. Profiles ũ(z) and α(z) of complementary amplitude and phase as a function of z were then established.

Just as in the preceding examples, the nature of the observed particles was confirmed by observation under microscope.

Figure 5A:
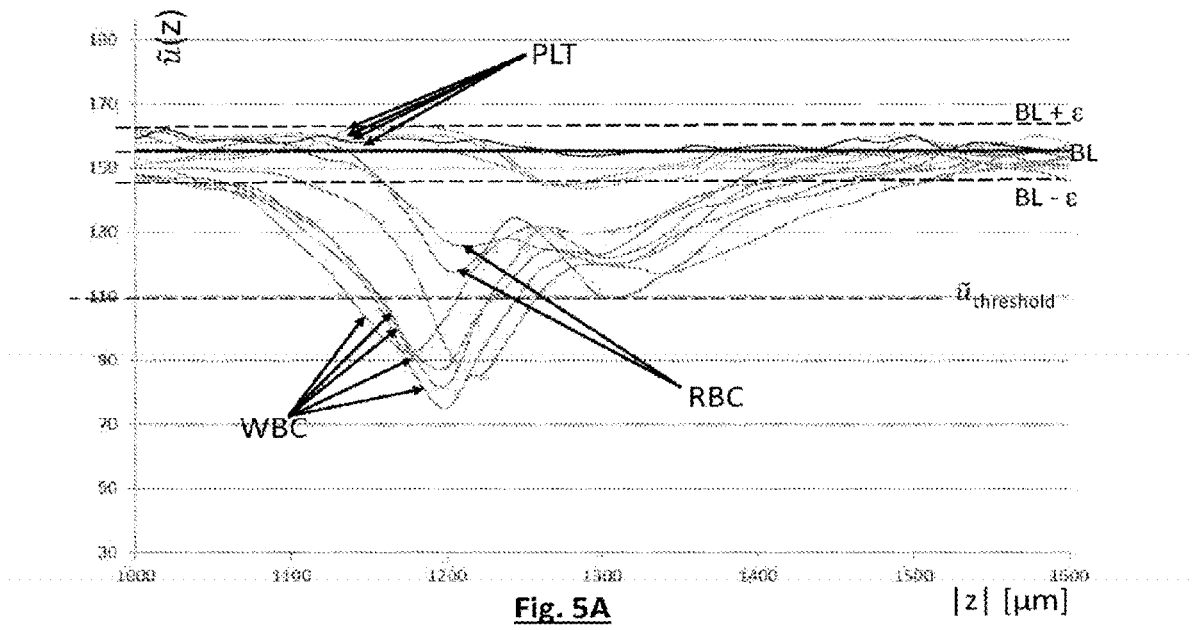
FIG. 5A shows the profile of a characteristic quantity, called the complementary amplitude, of the light wave to which the photodetector is exposed, as a function of distance with respect to the photodetector, for various types of particles, according to a second example.
Figure 5B:
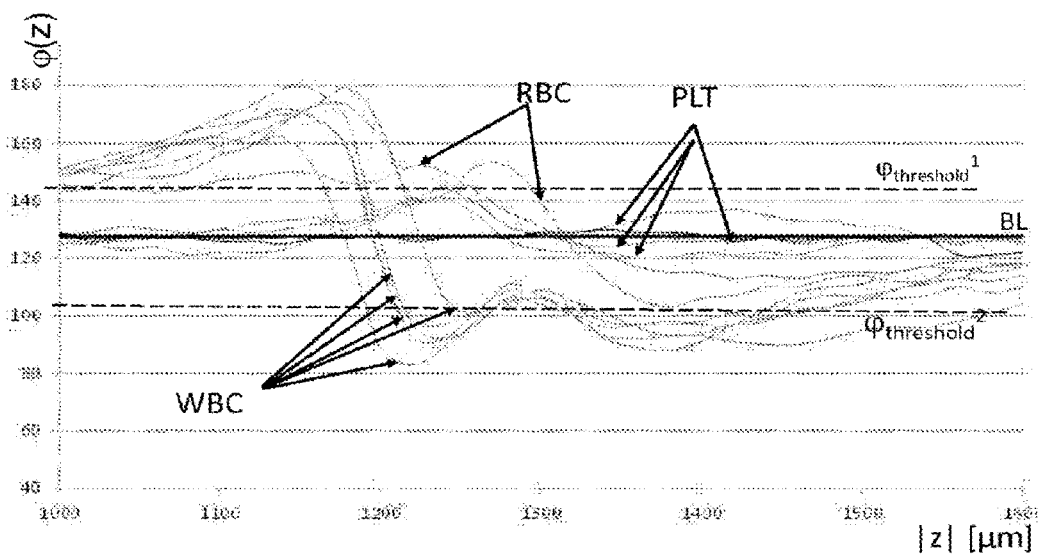
FIG. 5B shows the profile of the phase of the light wave to which the photodetector is exposed, as a function of distance z with respect to the photodetector, for various types of particles, according to a second example.

FIGS. 5A and 5B respectively show the complementary amplitude ũ(x,y,z) and phase φ(x,y,z) as a function of distance z for various particles. FIG. 5A shows that:

for particles corresponding to white blood cells WBC, the curve ũ (z) representing the variation in the complementary amplitude as a function of reconstruction distance has a marked minimum lower than an amplitude threshold $ũ_{threshold}$, followed by an increase toward the baseline BL, this increase having marked oscillations;

for particles corresponding to red blood cells RBC, the curve ũ (z) has a minimum comprised between the baseline BL and the amplitude threshold $ũ_{threshold}$, the curve then describing a monotonic increase to the baseline BL; and for particles corresponding to platelets PLT, the curve ũ(z) follows the baseline BL and remains confined between two values BL±ε.

Thus, for each detected particle n, the position of which in a plane parallel to the plane of the detector is ($x_n$,$y_n$), it is possible to establish a profile ũ($x_n$,$y_n$,z) representing the variation in the complementary amplitude ũ, such as defined above, of the wave 22 to which the detector is exposed, at a plurality of reconstruction heights z, and to use this profile to classify whether the particle is a red blood cell RBC, a white blood cell WBC or a platelet PLT.

Classification is therefore possible with a light source other than a laser source.

FIG. 5B shows that:

for particles corresponding to white blood cells WBC, the curve φ(z) representing the variation in the phase φ as a function of reconstruction distance z has a maximum higher than a first phase threshold $φ_{threshold}^1$, then a minimum lower than a second phase threshold $φ_{threshold}^2$, followed by an increase toward the baseline BL;

for particles corresponding to red blood cells RBC, the curve φ(z) has a maximum higher than said first phase threshold $φ_{threshold}^1$, then a minimum higher than said second phase $φ_{threshold}^2$, the curve then describing a monotonic increase toward the baseline BL; and for particles corresponding to platelets PLT, the curve φ(z) representing the variation in the phase φ as a function of reconstruction distance remains confined between the two values $φ_{threshold}^1$ and $φ_{threshold}^2$. The measured values remain between said first and second phase thresholds.

Thus, for each detected particle n, the position of which in a plane parallel to the plane of the detector is ($x_n$,$y_n$), it is possible to establish a profile φ($x_n$,$y_n$,z) representing the variation in the phase of the radiation to which the detector is exposed, at a plurality of reconstruction heights z, and to use this profile to classify whether the particle is a red blood cell, a white blood cell or a platelet.

In a third example, the light source 11 is a white light-emitting diode coupled to a 610-DF-20 Omega Optical filter centered on the wavelength λ=610 nm and of 20 nm full width at half maximum, said light source being placed at a distance Δ equal to 8 cm from the sample. The operating mode and sample are similar to those of the preceding example.

Figure 6A:
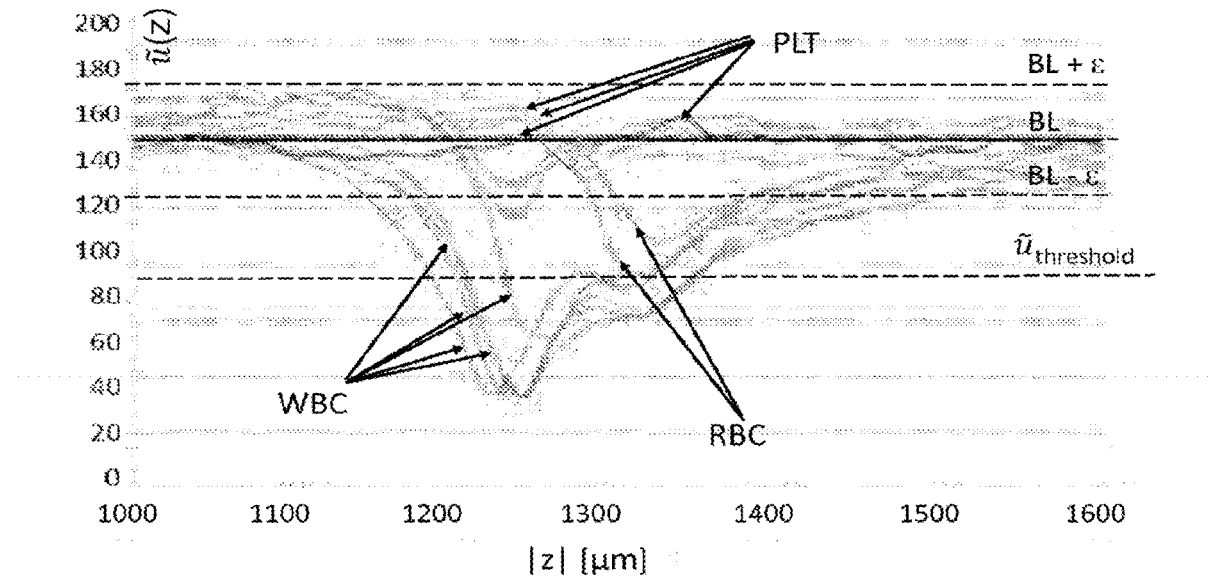
FIG. 6A shows the profile of a characteristic quantity, called the complementary amplitude, of the light wave to which the photodetector is exposed, as a function of distance with respect to the photodetector, for various types of particles, according to a third example.
Figure 6B:
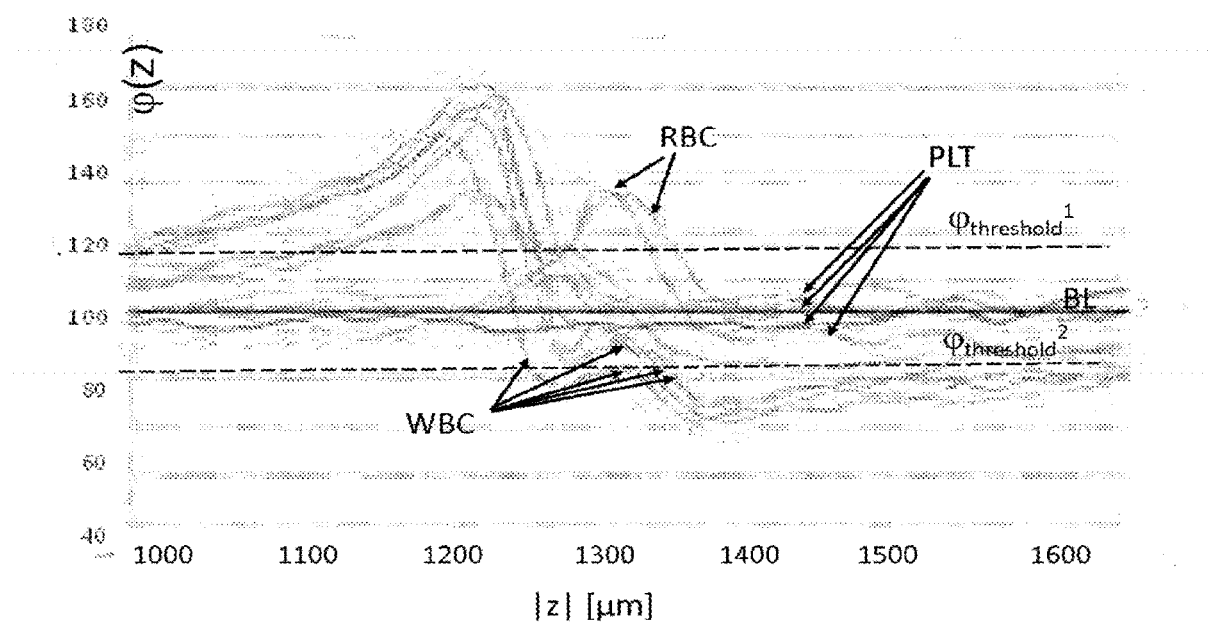
FIG. 6B shows the profile of the phase of the light wave to which the photodetector is exposed, as a function of distance with respect to the photodetector, for various types of particles, according to a third example.

FIGS. 6A and 6B respectively show the complementary amplitude ũ(x,y,z) and phase φ(x,y,z) as a function of distance z for various particles. FIG. 6A shows that:

for particles corresponding to white blood cells WBC, the curve ũ(z) representing the variation in the amplitude u as a function of reconstruction distance z has a marked minimum lower than a complementary amplitude threshold $ũ_{threshold}$, followed by an increase toward the baseline BL, this increase containing marked oscillations;

for particles corresponding to red blood cells RBC, the curve ũ(z) has a minimum comprised between the baseline BL and the amplitude threshold $ũ_{threshold}$, the curve then describing a monotonic increase to the baseline BL; and for particles corresponding to platelets PLT, the curve ũ(z) follows the baseline BL and remains confined between two values BL±ε.

Thus, for each detected particle n, the position of which in a plane parallel to the plane of the detector is ($x_n$,$y_n$), it is possible to establish a profile ũ($x_n$,$y_n$,z) representing the variation in the complementary amplitude, such as defined above, of the radiation to which the detector is exposed, at a plurality of reconstruction heights z, and to use this profile to classify whether the particle is a red blood cell RBC, a white blood cell WBC or a platelet PLT.

FIG. 6B shows that:

for particles corresponding to white blood cells WBC, the curve ((z) representing the variation in the phase p as a function of reconstruction distance z has a maximum higher than a first phase threshold $φ_{threshold}^1$, then a minimum lower than a second phase threshold $φ_{threshold}^2$, followed by an increase toward the baseline BL;

for particles corresponding to red blood cells RBC, the curve φ(z) has a maximum higher than said first phase threshold $φ_{threshold}^1$ then a minimum higher than said second phase threshold $φ_{threshold}^2$, the curve then describing a monotonic increase toward the baseline BL; and for particles corresponding to platelets PLT, the curve φ(z) representing the variation in the phase φ as a function of the reconstruction distance z remains confined between the two values $\varphi_{threshold}^1$, $\varphi_{threshold}^2$. The measured values remain between said first and second phase thresholds.

The two preceding examples show that a complementary-amplitude profile $\tilde{u}(z)$ or a phase profile $\varphi(z)$ allow particles to be characterized.

It is also possible to use what is called a composite optical parameter, symbol k, combining the complementary amplitude and phase, in the form of a ratio, for example $$k(z) = \frac{\varphi(z)}{\tilde{u}(z)}$$

Figure 7A:
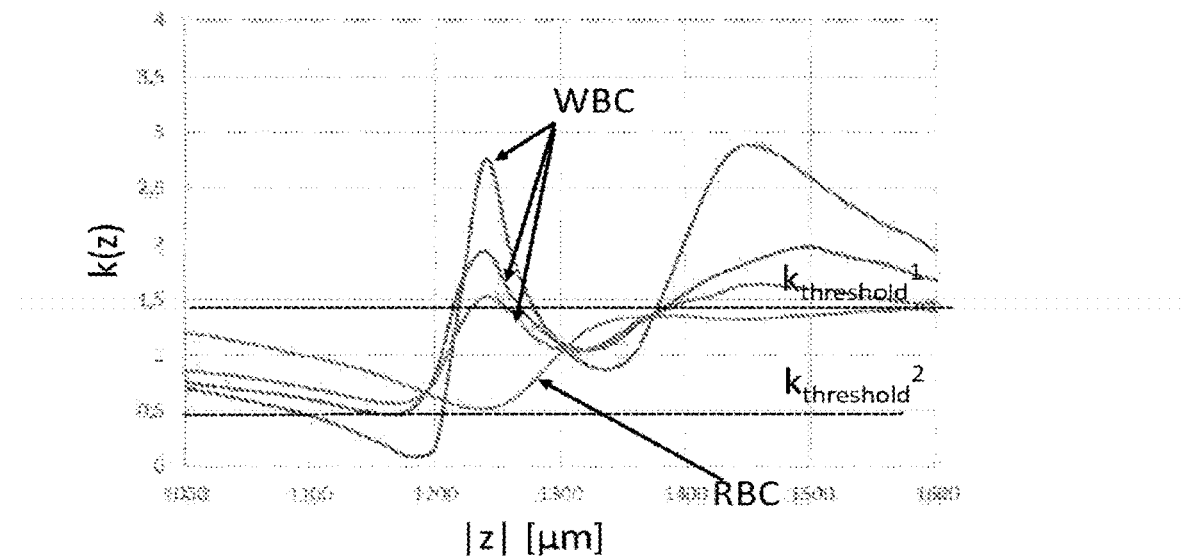
FIGS. 7A, 7B and 7C show the profile of a composite characteristic quantity of the light wave to which the photodetector is exposed, as a function of distance, according to the first, second and third examples, respectively.
Figure 7B:
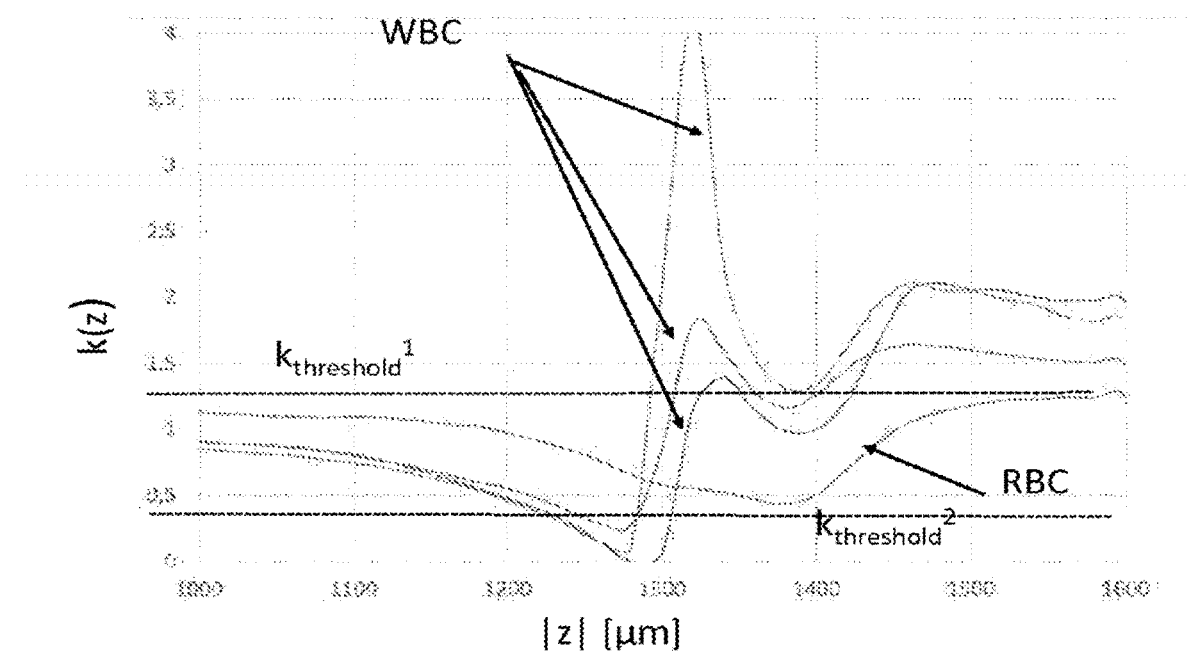
Figure 7C:
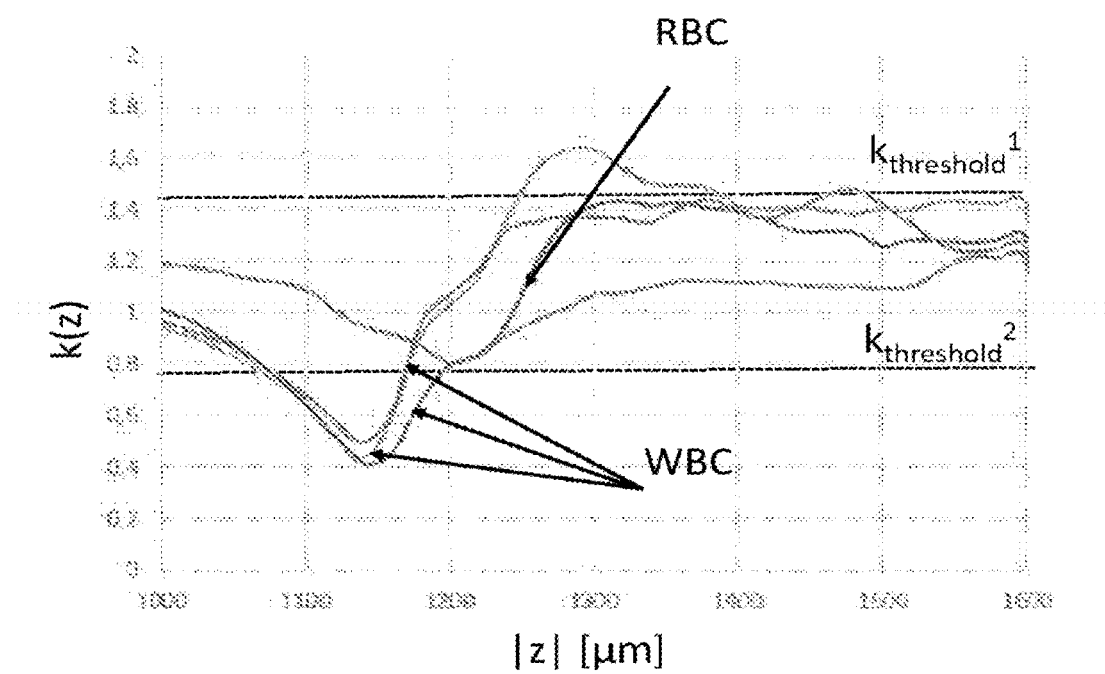

FIGS. 7A, 7B and 7C show the variation in said composite optical parameter along the propagation axis Z, in the configuration of the first example (405 nm laser source), of the second example (white LED light source combined with a filter centered on λ=485 nm) and of the third example (white LED light source combined with a filter centered on λ=610 nm). In each configuration the observed sample is a rich plasma such as described above.

In each graph, the analyzed particles are three white blood cells (WBC) and one red blood cell (RBC).

It may be seen that, whatever the source, the fluctuations in the profile k(z) are larger for white blood cells than for red blood cells.

In particular, it is possible to determine a first composite threshold $k_{threshold}^1$ and a second composite threshold $k_{threshold}^2$, such that, when the profile k(z) remains below the first composite threshold $k_{threshold}^1$ and above the second composite threshold $k_{threshold}^2$, the analyzed particle is a red blood cell. When the profile crosses one of these thresholds, the examined particle is identified as being a white blood cell.

Application of a digital propagation operator h to an image I, or hologram, acquired by a matrix-array photodetector 16 may have certain limits, because the acquired image includes no phase-related information. Thus, before the profile is established, it is preferable to obtain information relating to the phase of the light wave 22 to which the photodetector 16 is exposed. This phase-related information may be obtained by reconstructing a complex image $U_z$ of the sample 14, using methods described in the prior art, so as to obtain an estimation of the amplitude and phase of the light wave 22 in the plane P of the matrix-array photodetector 16 or in a reconstruction plane $P_z$ located at a distance |z| from the latter. The inventors have developed a method based on the calculation of a reference complex image, which method is described with reference to FIG. 8A. This method comprises the following steps:

Acquiring an image I of the sample 14 with the matrix-array photodetector 16, this image forming the hologram (step 100).

Calculating a complex image called the reference image $U_{ref}$ of the sample 14 in a reconstruction plane $P_z$ or in the detection plane P, this reference complex image including information on the phase and amplitude of the light wave 22 to which the matrix-array photodetector 16 is exposed; this step is carried out by applying the propagation operator h described above to the acquired image I (steps 110 to 170). This complex image is said to be a reference image because the formation of the profile on the basis of which the particle is characterized is based thereon.

Selecting a radial position (x,y) of a particle in the detection plane or in a plane parallel to the latter (step 180), either using the reference complex image $U_{ref}$ or the image I acquired by the photodetector 16.

Applying the propagation operator h to the reference complex image $U_{ref}$ so as to calculate complex images $U_{ref,z}$, called secondary images, along the propagation axis Z (step 185).

From each secondary complex image $U_{ref,z}$, estimating a characteristic quantity of the light wave 22, at the radial position (x,y) of the particle selected beforehand, and at a plurality of distances from the reconstruction plane $P_z$ (or from the detection plane P), and then forming a profile representing a variation in said characteristic quantity along the propagation axis Z (step 190).

Characterizing the particle depending on said profile. As indicated above, this characterization may be achieved by comparing the obtained profile with standard profiles obtained in a calibrating phase, using standard samples (step 200).

The algorithm presented in FIG. 8A is detailed below, the results obtained in certain steps being illustrated in FIGS. 8B to 8D. Steps 110 to 170 are a preferred way of obtaining a reference complex image, denoted $U_{ref}$, this image representing a spatial distribution of the complex expression of the wave 22 in a reconstruction plane $P_z$. Those skilled in the art will understand that other algorithms allow such a complex image to be reconstructed, it for example also being envisionable to use the algorithms mentioned with reference to the prior art.

Step 100: Image Acquisition

In this step, the image sensor 16 acquires an image I of the sample 14, and more precisely of the light wave 22 transmitted by the latter, to which light wave the image sensor is exposed. Such an image, or hologram, is shown in FIG. 8B.

This image was produced using a sample 14 including red blood cells immersed in a saline buffer, the sample being contained in a fluidic chamber of 100 µm thickness placed at a distance d of 1500 µm from a CMOS sensor, as in the device described above.

Step 110: Initialization

In this step, an initial image $U_0^{k=0}$ of the sample 14 is defined, from the image I acquired by the image sensor 16. This step is an initialization of the iterative algorithm described below with reference to steps 120 to 180, the exponent k indicating the rank of each iteration. The modulus $u_0^{k=0}$ of the initial image $U_0^{k=0}$ may be obtained by applying the square-root operator to the image I acquired by the image sensor, in which case $u_0^{k=0} = \sqrt{I_0}$. In this example, the image I is normalized by a term representative of the intensity of the light wave 12 incident on the sample 14. The latter may for example be the square root of a mean $\bar{I}$ of the image I, in which case each pixel I(x,y) of the acquired image is divided by said mean, such that $$u_0^{k=0} = \sqrt{\frac{I(x,y)}{\bar{I}}}$$

The phase $\varphi_0^{k=0}$ of the initial image $U_0^{k=0}$ is either considered to be zero in each pixel (x,y), or preset to an arbitrary value. Specifically, the initial image $U_0^{k=0}$ results directly from the image I acquired by the matrix-array photodetector 16. However, the latter includes no information relating to the phase of the light wave 22 transmitted by the sample 14, the image sensor 16 being sensitive only to the intensity of this light wave.

Step 120: Propagation

In this step, the image $U_0^{k-1}$ obtained in the plane of the sample is propagated to a reconstruction plane $P_z$, by applying a propagation operator such as described above, so as to obtain a complex image $U_z^k$, representative of the sample 14, in the reconstruction plane $P_z$. The propagation is carried out by convoluting the image $U_0^{k-1}$ with the propagation operator $h_{-z}$, such that:

$$U_z^k = U_0^{k-1} * h_{-z},$$

the symbol * representing a convolution operator. The index −z represents the fact that the propagation is carried out in a direction opposite to that of the propagation axis Z. Back-propagation is spoken of.

In the first iteration (k=1), $U_0^{k=0}$ is the initial image determined in step 110. In the following iterations, $U_0^{k-1}$ is the complex image in the detection plane P updated in the preceding iteration.

The reconstruction plane $P_z$ is a plane away from the detection plane P, and preferably parallel to the latter. Preferably, the reconstruction plane $P_z$ is a plane $P_{14}$ in which the sample 14 lies. Specifically, an image reconstructed in this plane allows a generally high spatial resolution to be obtained. It may also be a question of another plane, located a nonzero distance from the detection plane, and preferably parallel to the latter, for example a plane lying between the matrix-array photodetector 16 and the sample 14.

Step 130: Calculation of an Indicator in a Plurality of Pixels

In this step, a quantity $\varepsilon^k(x,y)$ associated with each pixel of a plurality of pixels (x,y) of the complex image $U_z^k$ is calculated, preferably in each of these pixels. This quantity depends on the value $U_z^k(x,y)$ of the image $U_z^k$, or of its modulus, in the pixel (x,y) for which it is calculated. It may also depend on a dimensional derivative of the image in this pixel, for example the modulus of a dimensional derivative of this image.

In this example, the quantity $\varepsilon^k(x,y)$ associated with each pixel is a modulus of a difference between the image $U_z^k$, in each pixel, and the value 1. Such a quantity may be obtained using the expression:

$$\varepsilon^k(x,y) = \sqrt{(U_z^k(x,y)-1)(U_z^k(x,y)-1)^*} = |U_z^k(x,y)-1|$$

Step 140: Establishment of a Noise Indicator Associated with the Image $U_z^k$

In step 130, quantities $\varepsilon^k(x,y)$ were calculated in a plurality of pixels of the complex image $U_z^k$. These quantities may form a vector $E^k$, the terms of which are the quantities $\varepsilon^k(x,y)$ associated with each pixel (x,y). In this step, an indicator, called the noise indicator, is calculated from a norm of the vector $E^k$. Generally, an order is associated with a norm, such that the norm $\|x\|_p$ of order p of a vector x of dimension n of coordinates $(x_1, x_2, \ldots, x_n)$ is such that: $\|x\|_p = (\sum_{i=1}^n |x_i|^p)^{1/p}$, where p≤0.

In the present case, a norm of order 1 is used, in other words p=1. Specifically, the inventors have estimated that a norm of order 1, or of order lower than or equal to 1, is particularly suitable for such a sample, as explained below.

In this step, the quantity $\varepsilon^k(x,y)$ calculated from the complex image $U_z^k$, in each pixel (x,y) of the latter, is summed so as to form a noise indicator $\varepsilon^k$ associated with the complex image. $U_z^k$.

Thus, $\varepsilon^k = \sum_{(x,y)} \varepsilon^k(x,y)$

Because a norm of order 1, or of order lower than or equal to 1, is used, the value of the noise indicator $\varepsilon^k$ decreases as the complex image $U_z^k$ becomes more and more representative of the sample. Specifically, in the first iterations, the value of the phase $\varphi_0^k(x,y)$, in each pixel (x,y) of the image $U_0^k$ is poorly estimated. Propagation of the image of the sample from the detection plane P to the reconstruction plane $P_z$ is then accompanied by substantial reconstruction noise, as mentioned with regard to the prior art. This reconstruction noise takes the form of fluctuations in the reconstructed image. Because of these fluctuations, a noise indicator $\varepsilon^k$, such as defined above, increases in value as the contribution of the reconstruction noise, in the reconstructed image, increases. Specifically, the fluctuations due to the reconstruction noise tend to increase the value of this indicator.

An important aspect of this step consists in determining, in the detection plane P, phase values $\varphi_0^k(x,y)$ for each pixel of the image of the sample $U_0^k$, this allowing, in a following iteration, a reconstructed image $U_z^{k+1}$ to be obtained the indicator $\varepsilon^{k+1}$ of which is lower than the indicator $\varepsilon^k$.

In the first iteration, as explained above, relevant information is available only on the intensity of the light wave 22, and not on its phase. The first image $U_z^{k=1}$ reconstructed in the reconstruction plane $P_z$ is therefore affected by a substantial amount of reconstruction noise, because of the absence of relevant information as to the phase of the light wave 22 in the detection plane P. Therefore, the indicator $\varepsilon^{k=1}$ is high. In following iterations, the algorithm carries out a gradual adjustment of the phase $\varphi_0^k(x,y)$ in the detection plane P, so as to gradually minimize the indicator $\varepsilon^k$.

The image $U_0^k$ in the detection plane is representative of the light wave 22 in the detection plane P, both from the point of view of its intensity and of its phase. Steps 120 to 160 aim to establish, iteratively, for each pixel of the image $U_0^k$, the value of the phase $\varphi_0^k(x,y)$ which minimizes the indicator $\varepsilon^k$, the latter being obtained from the image $U_z^k$ obtained by propagating the image $U_0^{k-1}$ to the reconstruction plane $P_z$.

The minimization algorithm may be a gradient descent algorithm, or a conjugated gradient descent algorithm, the latter being described below.

Step 150: Adjustment of the Value of the Phase in the Detection Plane.

Step 150 aims to determine a value of the phase $\varphi_0^k(x,y)$ of each pixel of the complex image $U_0^k$, so as to minimize, in the following iteration k+1, the indicator $\varepsilon^{k+1}$ resulting from a propagation of the complex image $U_0^k$ to the reconstruction plane $P_z$. To do this, a phase vector $\varphi_0^k$ is established, each term of which is the phase $\varphi_0^k(x,y)$ of a pixel (x,y) of the complex image $U_0^k$. The dimension of this vector is ($N_{pix}$, 1), where $N_{pix}$ is the number of pixels in question. This vector is updated in each iteration, using the following updating expression:

$$\varphi_0^k(x,y) = \varphi_0^{k-1}(x,y) + \alpha^k p^k(x,y) \text{ where:}$$

$\alpha^k$ is an integer, called the "step size", representing a distance;

$p^k$ is a direction vector, of dimension ($N_{pix}$, 1), each term p(x,y) of which forms a direction of the gradient $E\varepsilon^k$ of the indicator $\varepsilon^k$.

This equation may be expressed in vectorial form as follows:

$$\varphi_0^k = \varphi_0^{k-1} + \alpha^k p^k$$

It may be shown that:

$$p^k = -\nabla \varepsilon^k + \beta^k p^{k-1}$$

where:

$\nabla \varepsilon^k$ is a gradient vector, of dimension ($N_{pix}$, 1), each term of which represents a variation in the indicator $\varepsilon^k$ as a function of each of the degrees of freedom of the unknowns of the problem, i.e. the terms of the vector $\varphi_0^k$;

$p^{k-1}$ is a direction vector established in the preceding iteration;

$\beta^k$ is a scale factor applied to the direction vector $p^{k-1}$.

Each term $\nabla \varepsilon^k(x,y)$ of the gradient vector $\nabla \varepsilon$ is such that $$\nabla \varepsilon^k(r') = \frac{\partial \varepsilon^k}{\partial \varphi_0^k(r')} = \text{Im}(U_0^{k*})(r') \cdot \left( \frac{(U_z^k - 1)}{|U_z^k - 1|} * h_z \right)(r')$$

where Im is an operator returning the imaginary part of the operand and r' is a coordinate (x,y) in the detection plane.

The scale factor $\beta^k$ may be expressed such that:

$$\beta^{(k)} = \frac{\nabla \varepsilon^{(k)} \cdot \nabla \varepsilon^{(k)}}{\nabla \varepsilon^{(k-1)} \cdot \nabla \varepsilon^{(k-1)}}$$

The step size $\alpha^k$ may vary depending on the iteration, for example between 0.03 in the first iterations and 0.0005 in the last iterations.

The updating equation allows an adjustment of the vector $\varphi_0^k$ to be obtained, this leading to an iterative update of the phase $\varphi_0^k(x,y)$ in each pixel of the complex image $U_0^k$. This complex image $U_0^k$, in the detection plane, is then updated with these new values of the phase associated with each pixel. It will be noted that the modulus of the complex image $U_0^k$ is not modified, the latter being determined from the image acquired by the matrix-array photodetector 16, such that $u_0^k(x,y) = u_0^{k=0}(x,y)$.

Step 160: Reiteration of or Exit from the Algorithm.

Provided that a convergence criterion has not been reached, step 160 consists in reiterating the algorithm, with a new iteration of steps 120 to 160, on the basis of the complex image $U_0^k$ updated in step 150. The convergence criterion may be a preset number K of iterations, or a minimum value of the gradient $\nabla \varepsilon^k$ of the indicator, or a difference considered to be negligible between two consecutive phase vectors $\varphi_0^{k-1}$, $\varphi_0^k$. When the convergence criterion is reached, the estimation is considered to be a correct estimation of a complex image of the sample, in the detection plane P or in the reconstruction plane $P_z$.

Step 170: Obtainment of the Reference Complex Image.

At the end of the last iteration, the method may comprise propagating the complex image $U_0^k$ resulting from the last iteration to the reconstruction plane $P_z$, so as to obtain a reference complex image $U_{ref} = U_z^k$. Alternatively, the reference complex image $U_{ref}$ is the complex image $U_0^k$ resulting from the last iterations in the detection plane P. When the density of the particles is high, this alternative is however less advantageous because the spatial resolution in the detection plane P is lower than in the reconstruction plane $P_z$, in particular when the reconstruction plane $P_z$ corresponds to a plane $P_{14}$ in which the sample 14 lies.

FIG. 8C shows an image of the modulus $u_z^{k=8}$ of each pixel of the reference complex image $U_z^{k=8}$ obtained in a reconstruction plane $P_z$ after 8 iterations. The spatial resolution of this image allows a good identification of the radial coordinates (x,y) of each particle.

Step 180: Selection of Particle Radial Coordinates.

In this step, the radial coordinates (x,y) of a particle are selected from the reference image $U_{ref} = U_z^{k=30}$, for example from the image of its modulus $u_{ref} = u_z^{k=30}$ or from the image of its phase $\varphi_{ref} = \varphi_z^{k=30}$. As mentioned above, the expression radial coordinate designates a coordinate in the detection plane or in the reconstruction plane. It is also envisionable to carry out this selection on the basis of the hologram $I_0$ or on the basis of the complex image u obtained in the detection plane following the last iteration. However, when the number of particles increases, it is preferable to carry out this selection on the image formed in the reconstruction plane, because of its better spatial resolution, in particular when the reconstruction plane $P_z$ corresponds to the plane of the sample $P_{14}$. In FIG. 8C, the selection of a particle, which is encircled by a dotted outline, has been shown.

Step 185: Application of a Propagation Operator

In this step 185, the reference complex image $U_{ref}$ is propagated to a plurality of reconstruction distances, using a propagation operator h such as defined above, so as to obtain a plurality of what are called secondary complex images $U_{ref,z}$ reconstructed at various distances from the detection plane P or from the reconstruction plane $P_z$. Thus, this step comprises determining a plurality of complex images $U_{ref,z}$ such that:

$$U_{ref,z} = U_{ref} * h_z \text{ where } z_{min} \leq z \leq z_{max}.$$

The values $z_{min}$ and $z_{max}$ are the minimum and maximum coordinates, along the axis Z, to which the reference complex image is propagated. Preferably, the complex images are reconstructed at a plurality of coordinates z between the sample 14 and the image sensor 16. The complex images may be formed on either side of the sample 14.

These secondary complex images are established by applying a holographic reconstruction operator k to the reference image $U_{ref}$. The latter is a complex image correctly describing the light wave 22 to which the image sensor is exposed, and in particular its phase, following the iterations of the steps 120 to 160. Therefore, the secondary images $U_{ref,z}$ form a good descriptor of the propagation of the light wave 22 along the propagation axis Z.

Step 190: Formation of a Profile

In this step, from each secondary complex image $U_{ref,z}$, a characteristic quantity, such as defined above, of the light wave 22 is determined so as to define a profile representing the variation in said characteristic quantity along the propagation axis Z. The characteristic quantity may, for example, be the modulus or the phase, or a combination thereof. FIG. 8D shows the variation in the phase $\varphi(z)$ of the light wave 22 along the propagation axis Z.

Step 200: Characterization

The particle may then be characterized from the profile formed in the preceding step. Preferably, there is available a database of standard profiles formed in a learning phase using known standard samples. The characterization is then carried out by comparing or classifying the formed profile on the basis of the standard profiles.

This embodiment has been tested on samples including red blood cells. Another example is presented in FIGS. 9A to 9E. In these examples, the sample includes red blood cells diluted in an aqueous solution including a phosphate-buffered saline (PBS) buffer diluted to 1/400. The sample 14 was placed in a fluidic chamber 15 of 100 μm thickness, which chamber was placed at a distance of 8 cm from the light-emitting diode, described above, the spectral band of which was centered on 450 nm. The sample was placed at a distance of 1.5 mm from the CMOS image sensor described above. The aperture of the spatial filter 18 was 150 µm in size.

FIG. 9A shows the image I acquired by the image sensor. The images of the modulus and of the phase of the complex image $U_z^{k=8}$ reconstructed, in the plane $P_{10}$ of the sample, are shown in FIGS. 9B and 9C, respectively. These images were obtained in 8 iterations.

The image $U_z^{k=8}$ forms a reference image $U_{ref}$ to which the propagation operator h as described above was applied, so as to obtain a plurality of secondary complex images $A_{ref,z}$ along the propagation axis Z. Moreover, in the image of the modulus or in the image of the phase of the reference image, a red blood cell was identified, the latter being encircled by a dotted line in each of these images. The radial coordinates (x,y) of this red blood cell were extracted. From the secondary complex images $A_{ref,z}$, a profile u(z) representative of the modulus and a profile φ(z) representative of the phase of the light wave 22 reaching the image sensor 16 were formed. The value of each point of the profile is obtained by determining the modulus and phase of a respective secondary image at said radial coordinates. FIGS. 9D and 9E respectively show the profile of the modulus and of the phase of the red blood cell thus selected. The profile was determined between the coordinates $z_{min}=1000$ µm and $z_{max}=2000$ µm with a z-wise step size of 5 µm. The reconstruction plane is located at 1380 µm from the detection plane, this corresponding to the abscissa 76 in FIGS. 9D and 9E.

The described method is not limited to blood and may be applied to other bodily fluids, for example urine, cerebrospinal fluid, bone marrow, etc. Moreover, the method may apply to non-bodily liquids, in particular for the analysis of pollutants or toxins in water or any other aqueous solution.

The method also applies to the detection and identification of particles placed in a non-liquid medium, for example an agar or the dry residue of a bodily liquid, for example a blood smear leading to an extensive deposit of dry blood on a slide. In the latter case, the particles are isolated from one another by dry residues or air.

Moreover, as indicated above, the particles may be endogenous (for example blood particles) or exogenous (microbeads, droplets).

The examples described above provide simple identification criteria based on the variation in the profile of a characteristic quantity as a function of reconstruction distance, and on comparisons using preset thresholds. The validity of the criteria is related to the medium in which the particles are placed, and to the preparation protocol of the sample. Other criteria may apply to particles having undergone a different preparation protocol. Thus, for a given type of sample, the identification criteria may be defined in a learning phase, carried out on standard samples, including known particles.

In addition, other classifying methods that are more complex and more robust may be implemented, without departing from the scope of the invention.

The invention claimed is:

1. A method for identifying a particle contained in a sample, the method comprising:
   a) illuminating the sample using a light source, the light source producing an incident light wave propagating towards the sample along a propagation axis;
   b) acquiring, using a matrix-array photodetector, an image of the sample, the sample being placed between the light source and the matrix-array photodetector such that the matrix-array photodetector is exposed to a light wave comprising interference between the incident light wave and a diffraction wave produced by the particle;
   c) determining a position of the particle in a plane parallel to a plane in which the matrix-array photodetector lies;
   d) applying, by a processor, a digital reconstruction algorithm to the acquired image, to estimate at least one characteristic quantity of the light wave to which the matrix-array photodetector is exposed, at a plurality of reconstruction distances from the matrix-array photodetector;
   e) determining, by the processor, a profile, representing a variation of the characteristic quantity as a function of the reconstruction distance, along an axis parallel to the propagation axis and passing through the position; and
   f) identifying the particle depending on the profile determined by the processor.

2. The method of claim 1, wherein the characteristic quantity is obtained by estimating, at each reconstruction distance, a complex expression of the light wave to which the matrix-array photodetector is exposed.

3. The method of claim 2, wherein the characteristic quantity is determined from the modulus or the argument of the complex expression.

4. The method of claim 2, wherein the position of the particle, in a plane parallel to the plane of the matrix-array photodetector, is determined using the image acquired by the matrix-array photodetector or using the complex expression of the light wave to which the matrix-array photodetector is exposed.

5. The method of claim 1, wherein the identification is achieved by comparing the variation of the characteristic quantity to reference profiles, the reference profiles being determined in a learning phase.

6. The method of claim 1, further comprising:
   determining a reference complex image, in a reconstruction plane or in the detection plane, by applying a digital reconstruction algorithm to the image acquired by the matrix-array photodetector;
   from the reference complex image, estimating at least one characteristic quantity of the light wave to which the matrix-array photodetector is exposed, at a plurality of reconstruction distances from the matrix-array photodetector.

7. The method of claim 6, further comprising:
   applying a propagation operator to the reference complex image, to calculate secondary complex images for a plurality of distances either from the reconstruction plane or from the plane in which the matrix-array photodetector lies;
   determining a characteristic quantity, at each of the distances, from each secondary complex image.

8. The method of claim 1, wherein the light source is a spatially coherent source.

9. The method of claim 1, wherein the light source is a light-emitting diode or a laser diode.

10. The method of claim 1, wherein no magnifying optics are placed between the sample and the matrix-array photodetector.

11. The method of claim 1, wherein the particle is a blood cell.

12. The method of claim 1, wherein the particles are identified among cell lines of white blood cells or red blood cells or platelets.

13. A device for identifying a particle, the particle being contained in a sample, the device comprising:

a light source configured to produce an incident light wave, along a propagation axis, in a direction of the sample; and a holder, for holding the sample between the light source and a matrix-array photodetector;

the matrix-array photodetector configured to acquire an image of the sample, on being exposed to a light wave resulting from interference between the incident light wave and a diffraction wave formed by the particle; and a processor configured to determine a position of the particle in a plane parallel to a plane in which the matrix-array photodetector lies;

apply a digital reconstruction algorithm to the acquired image, to estimate at least one characteristic quantity of the light wave to which the matrix-array photodetector is exposed, at a plurality of reconstruction distances from the matrix-array photodetector;

determine a profile, representing the variation of the characteristic quantity as a function of the reconstruction distance, along an axis parallel to the propagation axis and passing through the position such that the particle is identifiable based on the profile.

14. The device of claim 13, wherein the device comprises no magnifying optics between the matrix-array photodetector and the sample.

15. The device of claim 13, wherein the processor is further configured to:

determine, at each reconstruction distance, a complex expression of the optical radiation to which the detector is exposed; and estimate the characteristic quantity, at each reconstruction distance, by determining the modulus or argument of the complex amplitude.

* * * * *